United States Patent [19]

Kubota et al.

[11] Patent Number: 4,681,435
[45] Date of Patent: Jul. 21, 1987

[54] CONTACT PATTERN OBSERVATION APPARATUS

[75] Inventors: Kazuhisa Kubota; Shigekazu Yasuda, both of Aichi, Japan

[73] Assignee: Kabushiki Kaisha Tokai Rika Denki Seisakusho, Aichi, Japan

[21] Appl. No.: 595,339

[22] Filed: Mar. 30, 1984

[30] Foreign Application Priority Data

Mar. 31, 1983 [JP] Japan ............................ 58-47435[U]

[51] Int. Cl.⁴ .............................................. G06K 9/20
[52] U.S. Cl. ......................................... 356/71; 354/62
[58] Field of Search ......................... 356/71, 388-393; 382/4; 350/286, 421; 354/62

[56] References Cited

U.S. PATENT DOCUMENTS

| | | | |
|---|---|---|---|
| 1,931,992 | 10/1933 | Newcomer | 350/421 |
| 2,810,323 | 10/1957 | Coleman | 350/286 X |
| 2,821,111 | 1/1958 | Coleman | 350/286 X |
| 3,174,414 | 3/1965 | Myer | 356/71 X |
| 3,200,701 | 8/1965 | White | 356/71 X |
| 3,482,498 | 12/1969 | Becker | 382/4 X |
| 3,527,535 | 9/1970 | Monroe | 356/71 |
| 3,856,380 | 12/1974 | Krishnan | 350/286 X |
| 3,947,128 | 3/1976 | Weinberger et al. | 356/71 |
| 3,975,711 | 8/1976 | McMahon | 356/71 X |

OTHER PUBLICATIONS

Follette et al., "Direct Optical Input System for Fingerprint Verification", IBM Tech. Disclosure, vol. 16, No. 11, Apr. 1974, pp. 3572-3573.
Kingslake, "Applied Optics and Optical Engineering", vol. V, Optical Instruments Part II, 1969, pp. 8-10.

*Primary Examiner*—Vincent P. McGraw
*Attorney, Agent, or Firm*—Finnegan, Henderson, Farabow, Garrett and Dunner

[57] ABSTRACT

An object contact pattern observation apparatus includes a prism body having a detection portion and a light absorbing portion located in such positions that any light transmitted through the prism body when no object is in contact with the detection portion. When an object is in contact with the detection portion, light from a light source radiated through the prism body to illuminate the detection portion is reflected therefrom as a visible contact image. The visible contact image is focused on a light recording device by a lens.

3 Claims, 3 Drawing Figures

CONTACT PATTERN OBSERVATION APPARATUS

FIELD OF THE INVENTION

The present invention relates to a contact pattern observation apparatus for observing a contact pattern at a contact position when an opaque body is urged thereto.

BACKGROUND OF THE INVENTION

A contact pattern apparatus is used when a fingerprint is photographed, when a contact portion of the sole of foot in the upright state is observed and in similar applications. Any of the conventionally proposed contact pattern devices, however, has a probelm in that sufficient contrast ratio cannot be obtained. As a result, it is difficult to perform the observation.

OBJECTS AND SUMMARY OF THE INVENTION

It is an object of the present invention to improve the contrast ratio in a contact pattern observation apparatus.

Another object of the present invention is to prevent ambient light around a contact area from reducing the background contrast ratio in a contact pattern observation apparatus.

A further object of the present invention is an inexpensive contact pattern observation apparatus providing high quality images of contact patterns.

These and other objects are achieved by a contact pattern observation apparatus comprising a transparent body having a substantially planar detection portion and a light absorbing portion provided at a position onto which external light impinging on the external surface of said detection portion is substantially totally reflected, and a light source for radiating light through the transparent body to the detection portion whereby when an object to be observed is placed in contact with the external surface of the detection portion the light from the light source reflected from the object forms a visual contact image superimposed on the light absorbing background to obtain a clean contact pattern with a high contrast ratio.

DETAILED DESCRIPTION OF THE PREFERRED EMBODIMENTS

Figure 1:
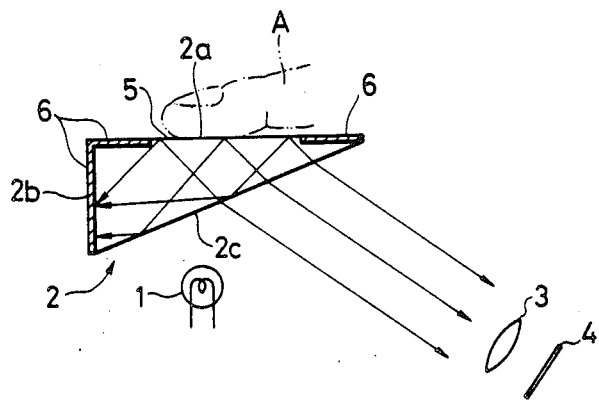
FIG. 1 illustrates a first embodiment of the present invention.

As shown in FIG. 1, a light source 1, such as a lamp, projects light toward a transparent body. As embodied herein, the transparent body comprises a triangular prism 2 having a detection portion 5 formed at a central portion of a surface 2a. A light absorbing portion 6 is formed by a blackening process applied to a surface 2b which is perpendicular to the surface 2a and to the periphery of the surface 2a. The prism 2 further includes a surface 2c which is inclined with respect to the surfaces 2a and 2b.

Ambient light which impinges upon the external surface of the detection portion 5 or upon the external surface of the surface 2c and is transmitted into the prism 2 is totally reflected to the surface 2b and absorbed by the light absorbing portion 6. The external surface of the detection portion 5 is adapted for contact with an opaque elastic body A such as a fingertip, the sole of a foot, gum-like material, etc. When an opaque elastic body A is in contact with the detection portion 5, the light from the light source 1 enters the prism 2 through the surface 2c and is radiated from the detection portion 5 onto the body A.

The light reflected from the body A comprises a visual image of the contact pattern of the body A and the detection portion 5. The visual image is transmitted from the surface 2c of the prism 2 and passes through a lens 3 before being captured by a light receiving element 4. The lens 3 and the light receiving element 4 are disposed in a position at which the light absorbing portion 6 of the surface 2b reflected at the detection portion 5 through the surface 2c can be observed. That is, the lens 3 and the light receiving element 4 are located in the optical path of light totally reflected at the detection portion 5. Accordingly, ambient light entering the prism 2 through the detection portion 5 does not reach the light receiving element 4. Practical examples of the light receiving element 4 includes a Cds, a photo transistor, a CCD, etc.

When no observed body A is in contact with the detection portion 5, the light from the light source 1 is absorbed by the light absorbing body 6 of the surface 2b and the light entering the prism 2 from the detection portion 5 cannot reach the light receiving element 4. In this state, the light receiving element 4 receives no light at all.

If an opaque body A is placed in contact with the detection portion 5, the condition of total reflection cannot be held at the detection portion 5. The light from the light source 1 is reflected from the opaque body A as a visual contact image which passes through the prism 2 and is focused on the light receiving element 4 by the lens 3. Thus a visual image of the contact pattern of the opaque body A is observed. The contrast ratio of this contact pattern is high and the contact pattern is clear because the contact pattern is projected with the light absorbing portion 6 of the surface 2b as a background and is not affected by external light at all.

Figure 2:
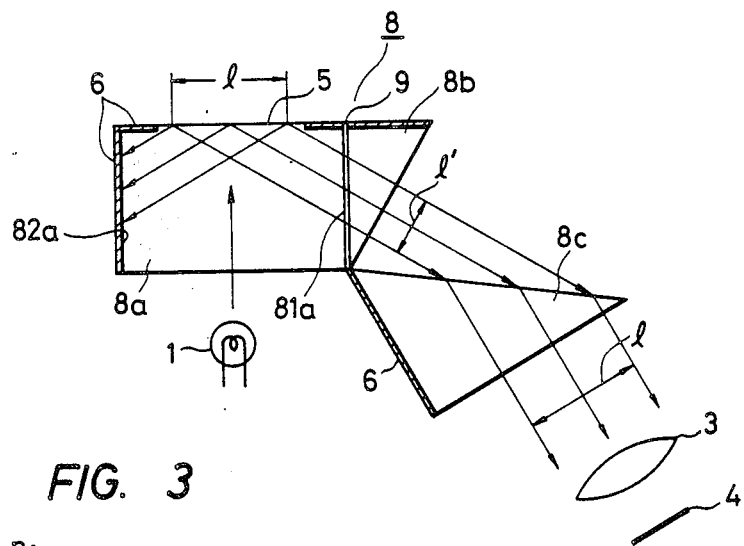
FIG. 2 illustrates a second embodiment of the present invention.

FIG. 2 illustrates a second embodiment of the present invention. In this second embodiment, a prism 8 is constituted by a rectangular prism piece 8a and triangular prism piece 8b and 8c. An air gap 9 is provided between the prism pieces 8a and 8b to intercept external light.

Figure 3:
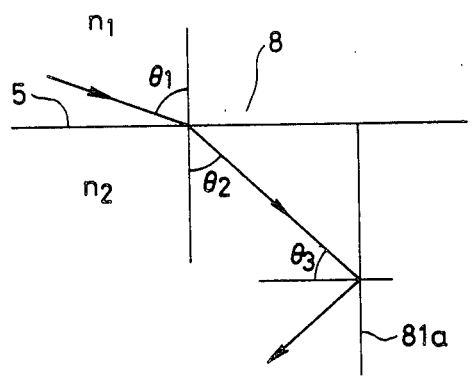
FIG. 3 is a schematic diagram illustrating physical properties of light reflection.

Ambient light entering the prism piece 8a through the external surface of a detection portion 5 does not exceed a critical angle at the detection portion with the result that the external light is totally reflected at the boundary surface between a surface 81a of the prism piece 8a and the air gap portion 9. This prevents the external light from entering the prism piece 8b if the refractive index of the prism 8 is properly set. This function is described in detail by referring to FIG. 3. In accordance with the law of refraction, the following relation holds:

$$n_1 \sin \theta_1 = n_2 \sin \theta_2$$

where $n_1$ and $n_2$ represent the refractive indices of air and the prism piece 8a, respectively. The angle $\theta_1$ represents the angle of incidence of external light to the prism piece 8a, and the angle $\theta_2$ represents the refractive angle when this external light passes through the prism piece 8a.

Let the refractive index of air be 1 and $\theta_1 = 90°$, the critical angle in the prism 8 is obtained as follows:

$$\sin 90° = n_2 \sin \theta_2$$

$$\therefore \sin \theta_2 = 1/n_2$$

$$\therefore \text{critical angle} = \sin^{-1} 1/n_2$$

That is, the refractive angle $\theta_2$ of the external light is as follows even if the external light enters at any angle of incidence:

$$\theta_2 < \sin^{-1} 1/n_2$$

In order to totally reflect the entering light at the surface 81a, the following relation holds:

$$\sin^{-1} 1/n_2 < \theta_3$$

where the angle $\theta_3$ represents the angle between the light incident to the prism piece 8a and a normal to the surface 81a.

$$\therefore \theta_2 < \sin^{-1} 1/n_2 < \theta_3 \quad (1)$$

Since the surface 81a is perpendicular to the boundary surface between the detection portions 5 and the air outside, $$\theta_2 + \theta_3 = 90° \quad (2)$$

From the equation (1), $$\theta_2 < \theta_3 \quad (3)$$

From the equation (2), $$\theta_3 = 90° - \theta_2$$

Substituting this into the equation (3), $$\theta_2 < 90° - \theta_2$$

$$\therefore \theta_2 < 45°$$

Similarly, the following relation is obtained:

$$\theta_2 < 45° < \theta_3$$

Accordingly, if the critical angle is smaller than 45°, and angle $\theta_2$ is smaller than 45°, and the angle $\theta_3$ becomes larger than 45°, that is, larger than the critical angle, so that external light is totally reflected at the surface 81a.

From the condition that the critical angel = $\sin^{-1} 1/n_2 < 45°$, $n_2 < 1.414$ is obtained, and therefore all the external entering light can be totally reflected at the surface 81a if the refractive index of the prism 6 is selected to be larger than 1.414.

The prism piece 8c is for correcting the distortion of the visual image of the contact pattern. That is, since the image coming out of the prism piece 8b has been compressed from 1 to 1', it is expanded to 1 through the prism piece 8c. Thus, a visual image of the contact pattern at the detection portion 5 can be focused onto the light receiving element 4. The light absorbing portion 6 is also provided at each of the prism pieces 8b and 8c. The light absorbing portion 6 provided at the surface 82a of the prism piece 8a serves as the background of the contact pattern image.

Although the light absorbing portion 6 is formed by a blackening process in the embodiments described above, it is not limited to black color but may be a green or a red color body. Any color will do so long as it may be used as the background of the contact pattern image. Also, a camera may be used in place of the light receiving element 4 or the observation may be performed with the naked eye. In the foregoing embodiment, a lamp is used as the light source 1 but any other means for emitting the light may be used as the light source 1. For example, a natural key of light such as sunshine and other artificial lights may be used.

The present invention can be used for photographing a fingerprint, a fish print, for checking the contact position of an elastic body (such as gum) under the urged condition, for observing the degree of contact of the sole of a foot in the upright state, etc. Further, it can be applied to a fingerprint detection type keyless entry system. In summary, it can be widely used for the observation of the contact condition of an opaque body which has some elasticity.

While the salient features of the invention have been described with reference to the drawings, it should be understood that the preferred embodiments described herein are susceptible of modification and alteration without departing from the spirit and scope of the following claims.

We claim:

1. An object contact pattern observation apparatus comprising:

a transparent body comprising a prism, including a rectangular prism piece and a first triangular prism piece, said rectangular prism piece and said first triangular piece having respective mutually parallel planar surfaces extending substantially coextensively and being separated by an air gap, said air gap being provided to prevent ambient light entering said rectangular prism piece through a substantially planar detection portion from being transmitted into said first triangular prism piece; said rectangular prism piece additionally having a first surface and a second surface and said substantially planar detection portion being located on said first surface, a light absorbing portion located where light totally reflected at said detection portion is introduced to said light absorbing portion with said light absorbing portion including said second surface of said rectangular prism piece; a source for radiating light through said rectangular prism piece to said detection portion to form a visible contact image of a contact pattern of an object placed in substantial contact with said detection portion, said visible contact image appearing to be superimposed on said light absorbing portion and being transmitted from said rectangular prism piece to said first triangular prism piece and said image emerging from said first triangular prism piece in a reduced size with respect to the actual area of the substantial contact between the object and said detection portion; and a second triangular prism piece for receiving and restoring said visible contact image to the size of the actual area of the substantial contact between the object and said detection portion said restored image emerging from said second triangular prism piece for observation.

2. An object contact pattern observation apparatus according to claim 1 wherein the index of refraction of said rectangular piece prism is larger than 1.414.

3. An object contact pattern observation apparatus according to claim 1 further including:
 a light receiving element; and
 a lens for focusing said visible contact image on said light receiving element.

* * * * *

UNITED STATES PATENT AND TRADEMARK OFFICE
CERTIFICATE OF CORRECTION

PATENT NO. : 4,681,435

DATED : July 21, 1987

INVENTOR(S) : Kazuhisa Kubota et al.

It is certified that error appears in the above-identified patent and that said Letters Patent is hereby corrected as shown below:

Claim 2, column 5, line 6, "piece prism" should be --prism piece--.

Signed and Sealed this

Tenth Day of November, 1987

Attest:

DONALD J. QUIGG

*Attesting Officer*   *Commissioner of Patents and Trademarks*